United States Patent
Pinchuk

(10) Patent No.: US 8,155,759 B2
(45) Date of Patent: Apr. 10, 2012

(54) PACEMAKER LEAD AND METHOD OF MAKING SAME

(75) Inventor: Leonard Pinchuk, Miami, FL (US)

(73) Assignee: Innovia, LLC, Miami, FL (US)

( * ) Notice: Subject to any disclaimer, the term of this patent is extended or adjusted under 35 U.S.C. 154(b) by 82 days.

(21) Appl. No.: 12/690,997

(22) Filed: Jan. 21, 2010

(65) Prior Publication Data

US 2010/0241208 A1 Sep. 23, 2010

Related U.S. Application Data

(60) Provisional application No. 61/161,794, filed on Mar. 20, 2009.

(51) Int. Cl.
*A61N 1/00* (2006.01)
(52) U.S. Cl. ........................................ 607/119
(58) Field of Classification Search .............. 607/119, 607/116; 424/422
See application file for complete search history.

(56) References Cited

U.S. PATENT DOCUMENTS

| | | | |
|---|---|---|---|
| 4,269,198 A | 5/1981 | Stokes |
| 4,484,586 A | 11/1984 | McMickle et al. |
| 4,798,864 A | 1/1989 | Topcik |
| 4,975,207 A | 12/1990 | Lee |
| 5,259,395 A | 11/1993 | Li |
| 5,419,921 A | 5/1995 | Molacek et al. |
| 5,423,881 A | 6/1995 | Breyen et al. |
| 5,741,331 A | 4/1998 | Pinchuk |
| 5,852,118 A | 12/1998 | Horrion et al. |
| 5,854,347 A | 12/1998 | Laurin et al. |
| 6,167,314 A | 12/2000 | Fischer, Sr. et al. |
| 6,174,959 B1 | 1/2001 | Ciebien et al. |
| 6,218,475 B1 | 4/2001 | Hiro et al. |

(Continued)

OTHER PUBLICATIONS

"Medical Applications of Poly(Styrene-Block-Isobutylene-Block-Styrene) ("SIBS")," Pinchuk et al, Biomaterials (2007), doi:10.1016/j.biomaterials.2007.09.041.

*Primary Examiner* — George Manuel
*Assistant Examiner* — Robert Wieland
(74) *Attorney, Agent, or Firm* — Gordon & Jacobson, PC

(57) ABSTRACT

An improved pacemaker lead including a lead body supporting at least one flexible conductor element that provides an electrical signal path between a proximal connector element and a distal electrode. The lead body includes an insulating structure that protects the flexible conductor element(s) wherein the insulating structure is realized from a polymer blend of a thermoplastic polyurethane elastomer and an isobutylene block copolymer. The mole fraction of the isobutylene block copolymer of the polymer blend is in the range of 2-15% (most preferably on the order of 10%). The polymer blend of the insulating structure has a maximum tensile strength in the range of 20-40 MPa (most preferably in a range of 25-35 MPa). In the preferred embodiment, the hardness of the polymer blend can be characterized by a Shore hardness in a range of 70-80 A. The flexible conductor element(s) preferably include a coiled wire conductor defining a central axis with an outer surface facing radially outward away from the central axis and an inner surface facing radially inward toward the central axis, and the insulating structure surrounds at least the outer surface of the coiled wire conductor (and more preferably encapsulates the coiled wire conductor). The polymer blend of the insulating structure has reduced oxygen permeability, and thus provides improved resistance to environmental stress cracking and metal ion induced oxidation while maintaining the flexibility and desired tensile strength of the lead body.

19 Claims, 1 Drawing Sheet

U.S. PATENT DOCUMENTS

| | | |
|---|---|---|
| 6,306,177 B1 | 10/2001 | Felt et al. |
| 6,319,985 B1 | 11/2001 | Bruning et al. |
| 6,400,992 B1 | 6/2002 | Borgersen et al. |
| 6,477,427 B1 | 11/2002 | Stolz et al. |
| 7,236,834 B2 | 6/2007 | Christopherson et al. |
| 7,555,349 B2 | 6/2009 | Wessman et al. |
| 2006/0293453 A1 | 12/2006 | Jiang et al. |
| 2009/0087607 A1 | 4/2009 | Noda et al. |
| 2010/0166820 A1* | 7/2010 | Boden et al. .................. 424/422 |
| 2011/0054581 A1* | 3/2011 | Desai et al. .................. 607/116 |

* cited by examiner

PACEMAKER LEAD AND METHOD OF MAKING SAME

CROSS-REFERENCE TO RELATED APPLICATIONS

This application claims benefits from U.S. Provisional Patent Application No. 61/161,794, filed Mar. 20, 2009, the contents of which are hereby incorporated herein by reference.

BACKGROUND OF THE INVENTION

1. Field of the Invention

This invention relates broadly to medical electrical leads for electrical stimulation or electrical sensing of body organs or tissues and their method of fabrication. More particularly, this invention relates to implantable cardiac leads for delivering electrical stimulation to the heart, e.g., pacing pulses and cardioversion/defibrillation shocks, and/or sensing the cardiac electrogram (EGM) or other physiologic data.

2. State of the Art

Implantable medical electrical stimulation and/or sensing leads (referred to herein as "pacemaker leads or lead(s)") are well known in the fields of cardiac stimulation and monitoring, including cardiac pacing and cardioversion/defibrillation. In these applications, a pacemaker or cardioverter/defibrillator implantable pulse generator (IPG) or a cardiac monitor is coupled to the heart through one or more of such leads. The proximal end of such leads is formed with a connector element which connects to a terminal of the IPG or cardiac monitor. The distal end of such leads includes a distal stimulation and/or sensing electrode that is fixated to tissue at the desired treatment site. A lead body extends between the distal and proximal ends. The lead body comprises one or more electrical conductors surrounded by an insulating outer sleeve. Each electrical conductor provides an electrical signal path between the proximal connector element (and the IPG or cardiac monitor coupled thereto) and the distal stimulation and/or sensing electrode. A lead having a single distal stimulation and/or sensing electrode is typically referred to as a unipolar lead. A lead having two or more distal stimulation and/or sensing electrodes is typically referred to as a bipolar (or a multi-polar) lead. The leads are typically implanted using an endocardial approach or an epicardial approach. The endocardial approach is the most common method. The epicardial approach is a less common method in adults, but more common in children.

In the endocardial approach, a local anesthetic is typically applied to numb an incision area of the chest (typically adjacent the collar bone) where one or more leads and the IPG or cardiac monitor are inserted. Each lead is inserted through the incision and into a vein, then guided through a transvenous pathway to the heart with the aid of fluoroscopy. The distal lead electrode is affixed to the heart muscle at the desired treatment site. The proximal connector element of the lead is coupled to the IPG or cardiac monitor, and the IPG or cardiac monitor is placed in a pocket created under the skin in the upper chest. The transvenous pathway can include a number of twists and turns, and the lead body can be forced against bony structures of the body that apply stress to it.

The epicardial approach requires open heart surgery wherein the distal lead electrode of one or more leads is affixed directly to the heart tissue at the desired treatment site, instead of inserting the lead(s) through a vein. The proximal connector element of the lead is coupled to the IPG or cardiac monitor, and the IPG or cardiac monitor is placed in a pocket created under the skin in the abdomen.

In all applications, the heart beats approximately 100,000 times per day or over 30 million times a year, and each beat stresses at least the distal portion of the lead body. The lead conductors and insulation are subjected to cumulative mechanical stresses, as well as material reactions as described below, that can result in degradation of the insulation or fractures of the lead conductors with untoward effects on device performance and patient well being.

In order to facilitate advancement through the transvenous pathway (for the endocardial approach) and minimize stress on the lead body (for all applications), flexible lead bodies have been developed using smaller diameter coiled wire conductors and flexible insulating materials, most notably polyurethane compositions. However, problems have been encountered as to the bio-stability of such lead materials. More particularly, it is acknowledged that there are a number of mechanisms for degradation of elastomeric polyurethane insulation of the lead body in vivo. One is environmental stress cracking (ESC), which is the generation of crazes or cracks in the polyurethane elastomer produced by the combined interaction of a medium capable of acting on the elastomer and a stress level above a specific threshold. Another is metal ion induced oxidation (MIO) in which polyurethane elastomers exhibit accelerated degradation from metal ions such as cobalt ions, chromium ions, molybdenium ions and the like which are used alone or in alloys in the conductive wire of the lead body.

The degradation mechanism of polyether urethanes was elucidated by Anderson's group at Case Western Reserve University (Cleveland, Ohio). They found that the carbon alpha to the ether of the polyether soft segment was oxidized to ester either by superoxide ($O_3$) produced by polymorphonuclear leucocytes (PMNs) and the like, or by metal ion contact of the polyurethane, as occurs on the inside of pacemaker lead insulators. Subsequent hydrolysis of the ester cleaves the macromolecule, and in the presence of flexion, cracks develop. Realizing that the ether groups were vulnerable, the inventor of the subject application introduced more biostable polycarbonate urethanes for implant applications, which were initially commercialized under the trade name Corethane™ by Corvita Corp. of Miami, Fla. and now commercialized under the name Bionate® by DSM PTG of Berkley, Calif.

The improved biostability of polycarbonate urethanes was confirmed by Stoke's group at Medtronic using the "Stokes Test", in which a tube of the material is stretched over a dumbbell-shaped mandrel and exposed to oxidizing and hydrolyzing chemicals, or is implanted in the body for a predetermined time. Materials that are readily susceptible to oxidation and hydrolysis crack in this model; significantly, the polycarbonate urethanes did not crack over the duration tested.

Although polycarbonate urethanes demonstrated superior biostability relative to polyether and polyester urethanes, they too eventually exhibited biodegradation as manifested by surface cracking The fractures were most noticeable in areas with large numbers of macrophages on histology. Importantly, Wilson's group (The Hospital for Sick Children, Toronto, Ontario) also observed that these degrading implants attracted a plethora of polymorphonuclear leukocytes, especially during the early weeks of implantation. Further, the cleaner the polycarbonate urethane (less extractables, washed surfaces), the more intense the inflammation. Further observations were the attraction of macrophages, foreign body giant cells and the phagocytosis of small "chunks" of polyurethane. Lastly, it was also observed upon careful examination that crack formation in microfilamentous grafts as early as 1 month after implantation. A summary of these finding was recorded in the article by Pinchuk et al. entitled "Medical applications of poly(styrene-block-isobutylene-block-styrene) ("SIBS")," Biomaterials (2007), doi:10.1016/j.biomaterials.2007.09.041. In summary, polyurethanes exhibit degradation with time with signs of the problem occurring within weeks of implantation. Degradation is due to oxidation, most likely by superoxide produced by phagocytes ("scavenger cells"); the more degradation, the greater number of scavenger cells that migrate to the site, the worse the degradation. The more oxygen that can penetrate the polyurethane, the more it degrades and similarly, the more water that absorbs into the polyurethane, the better the transport of oxygen and other substances, for example, hydrogen ion, that can degrade the polymer.

SUMMARY OF THE INVENTION

It is therefore an object of the invention to provide a pacemaker lead with an insulator having improved resistance to in vivo degradation.

It is another object of the invention to provide a pacemaker lead having excellent flexibility and mechanical properties.

In accord with one embodiment of the invention, a pacemaker lead includes a lead body supporting at least one flexible conductor element that provides an electrical signal path between a proximal connector element and a distal electrode. The lead body includes an insulating structure that protects the flexible conductor element(s), wherein the insulating structure is realized from a polymer blend of a thermoplastic polyurethane elastomer and an isobutylene block copolymer. The mole fraction of the isobutylene block copolymer of the polymer blend is in the range between 2% and 15% (most preferably on the order of 10%). The polymer blend of the insulating structure has a maximum tensile strength in the range between 20 MPa and 40 MPa (most preferably in a range between 25 MPa and 35 MPa). In the preferred embodiment, the hardness of the polymer blend can be characterized by a Shore hardness in a range between 70 A and 80 A.

In the preferred embodiment, the flexible conductor element(s) include a coiled wire conductor defining a central axis with an outer surface facing radially outward away from the central axis and an inner surface facing radially inward toward the central axis, and the insulating structure surrounds at least the outer surface of the coiled wire conductor (and more preferably encapsulates the coiled wire conductor).

The polymer blend of the insulating structure has reduced oxygen permeability, and thus provides improved resistance to environmental stress cracking and metal ion induced oxidation while maintaining the flexibility and desired tensile strength of the lead body.

In the preferred embodiment, the thermoplastic polyurethane elastomer of the polymer blend includes soft segments, an isocynate component, and an optional chain extender component. The soft segments can be selected from the group including polyesters, polyethers, aliphatics, polycarbonates and mixtures thereof. The soft segments can be macrodiols terminated with diols, triols, multiols, or combinations thereof. The soft segments can also be macroamines terminated with diamines, triamines, multiamines, or combinations thereof. The isocyanate component can include a diisocyanate selected from the group including methylene bisphenyldiisocyanate (MDI), hydrogenated methylenebisphenyl diisocyanage (HMDI), toluene diisocyanate (TDI) hexamethylene dissocyanate, isophorone diisocyanate, and the like. The optional chain extender components can be selected from the group including 1,4-butanediol, ethylene glycol, ethylene diamine, 1,6-hexanediol and the like.

The isobutylene block copolymer of the polymer blend preferably consists of a first polymer block component containing isobutylene-derived monomer units and a second polymer block component derived from a monomer component other than isobutylene. The second polymer block component can be at least one cation-polymerizable monomer selected from the group including aliphatic olefins, alicyclic olefins, aromatic vinyl compounds, dienes, vinyl ethers, silanes, vinylcarbazole, β-pinene, acenaphthylene and like monomers. In the preferred embodiment, the mole fraction of the second polymer block component as part of the isobutylene block copolymer is in the range of 15% to 45% (and more preferably in the range of 25% to 35%), and the mole fraction of the first polymer block component of the isobutylene block copolymer is in the range of 85% to 55% (and more preferably in the range of 75% to 65%). Moreover, the Shore hardness of the isobutylene block copolymer of the polymer blend is preferably between 70A and 90A (and more particularly on the order of 80A).

The isobutylene block copolymer of the polymer blend preferably has a block structure selected from the group including a diblock copolymer structure, a triblock copolymer structure, and a multiblock copolymer structure. More preferably, the isobutylene block copolymer of the polymer blend comprises a styrene-isobutylene-styrene triblock copolymer.

The polymer blend can be formed by melt mixing or mixing in solution.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1A:
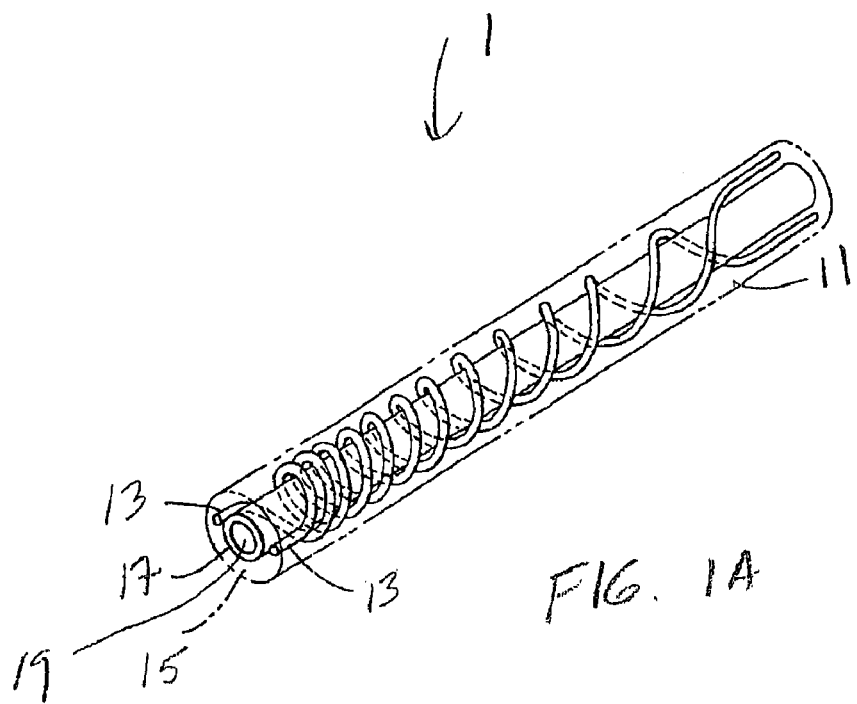
FIG. 1A is a perspective view of the body of an implantable pacemaker lead in which the present invention is embodied.
Figure 1B:
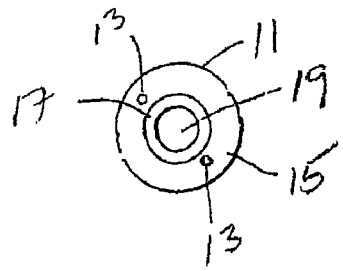
FIG. 1B is a cross-sectional view of the pacemaker lead body of FIG. 1A.
Figure 1C:
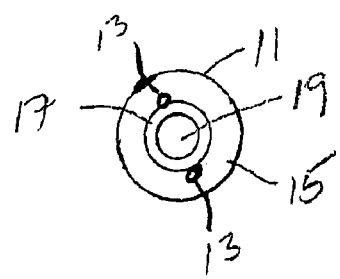
FIG. 1C is a cross-sectional view of a pacemaker lead body in accordance with another embodiment of the present invention.

Turning now to FIGS. 1A and 1B, a flexible pacemaker lead 1 is provided with a lead body 11 that includes one or more flexible conductor elements 13 surrounded by a coaxial insulating structure. The coaxial insulting structure includes an outer insulating part 15 and an inner insulating part 17 both realized from a polymer blend of a thermoplastic polyurethane elastomer and an isobutylene block copolymer. In the illustrative embodiment shown, the flexible conductor element 13 includes two coiled wire conductors. Each coiled wire conductor defines a central axis with an outer surface facing radially outward away from the central axis and an inner surface facing radially inward toward the central axis. The outer insulating part 15 encapsulates and insulates the coiled wire conductors 13 along the length of the lead body as best shown in the cross-section of FIG. 1B. Alternatively, the coiled wire conductors 13 can be encapsulated between the outer insulating part 15 and inner insulating part 17 as shown in FIG. 1C. In this configuration, the outer insulating part 15 surrounds the outer surface of the coiled wire conductors and the inner insulating part 17 surrounds the inner surface of the coiled wire conductors. In the preferred embodiment, the inner insulating part 17 defines a guide channel lumen 19 that removably receives a stylet that aids in maneuvering the lead body during implantation as is well known. The proximal end of lead body 11 includes a connector element (not shown) which connects to a terminal of the IPG or cardiac monitor. The distal end of the lead body 11 includes at least one distal stimulation and/or sensing electrode (not shown) that is fixated to cardiac tissue at the desired treatment site. The conductor element(s) 13 provide an electrical signal path between the proximal connector element (and the IPG or cardiac monitor coupled thereto) and the distal stimulation and/or sensing electrode(s).

The thermoplastic polyurethane elastomer of the polymer blend can be any type of polyurethane; e.g., any polyurethane with soft segments generally described as polyesters, polyethers, aliphatics, polycarbonates and mixtures thereof. The soft segments can be macrodiols terminated with diols, triols or multiols. In addition they can be macroamines terminated with diamines, triamines and multiamines and combinations thereof and in combination with diols. The thermoplastic polyurethane elastomer preferably includes an isocyanate component, which can be diisocyanates such as methylene bisphenyldiisocyanate (MDI), hydrogenated methylenebisphenyl diisocyanage (HMDI), toluene diisocyanate (TDI) hexamethylene dissocyanate, isophorone diisocyanate, and the like. The thermoplastic polyurethane elastomer also preferably includes chain extenders, which can be 1,4-butanediol, ethylene glycol, ethylene diamine, 1,6-hexandiol, etc. The resultant polyurethane or polyureas is the reaction product of a soft segment with a dissocyanate and with a chain extender (or it need not use a chain extender). The synthesis of such thermoplastic polyurethane elastomers is generally well-known in the art.

The isobutylene block copolymer of the blend is a block copolymer containing, in at least part thereof, isobutylene-derived monomer units and, in accordance with the present invention, it is constituted of a polymer block component (a) derived from isobutylene and a polymer block component (b) derived from a monomer component other than isobutylene. The polymer block component (a) may contain (or may not contain) a monomer component other than isobutylene. The monomer component other than isobutylene is not particularly restricted, and may be a cation-polymerizable monomer such as aliphatic olefins, alicyclic olefins, aromatic vinyl compounds, dienes, vinyl ethers, silanes, vinylcarbazole, β-pinene, acenaphthylene and like monomers. The monomer component constituting the polymer block component (b) may be a cation-polymerizable monomer such as:

- aliphatic olefins (e.g., ethylene, propylene, 1-butene, 2-methyl-1-butene, 3-methyl-1-butene, pentene, hexane, 4-methyl-1-pentene and octene), alicyclic olefins (e.g., cyclohexene, vinylcyclohexane and norbornene);
- aromatic vinyl monomers (e.g., styrene, o-, m- or p-methylstyrene, α-methylstyrene, β-methylstyrene, 2,6-dimethylstyrene, 2,4-dimethylstyrene, α-methyl-o-methylstyrene, α-methyl-m-methylstyrene, α-methyl-p-methylstyrene, β-methyl-o-methylstyrene, β-methyl-m-methylstyrene, β-methyl-p-methylstyrene, 2,4,6-trimethylstyrene, α-methyl-2,6-dimethylstyrene, α-methyl-2,4-dimethylstyrene, β-methyl-2,6-dimethylstyrene, β-methyl-2,4-dimethylstyrene, o-, m-, or p-chlorostyrene, 2,6-dichlorostyrene, 2,4-dichlorostyrene, α-chloro-o-chlorostyrene, α-chloro-m-chlorostyrene, α-chloro-p-chlorostyrene, β-chloro-o-chlorostyrene, (β-chloro-m-chlorostyrene, β-chloro-p-chlorostyrene, 2,4,6-trichlorostyrene, α-chloro-2,6-dichlorostyrene, α-chloro-2,4-dichlorostyrene, β-chloro-2,6-dichlorostyrene, β-chloro-2,4-dichlorostyrene, o-, m-, or p-t-butylstyrene, o-, m-, or p-methoxystyrene, o-, m-, or p-chloromethylstyrene, o-, m-, or p-bromomethylstyrene, silyl-substituted styrene derivatives, indene, and vinyl naphthalene);
- dienes (e.g., butadiene, isoprene, hexadiene, cyclopentadiene, cyclohexadiene, dicyclopentadiene, divinylbenzene, and ethylidenenorbornene);
- vinyl ethers (e.g., ethers having a vinyl group as well as ethers having a substituted vinyl group such as propenyl group, including methylvinylether, ethylvinylether, (n- or iso)propylvinylether, (n-, sec-, tert-, or iso)butylvinylether, methylpropenylether, and ethylpropenylether);
- silanes (e.g., vinyltrichlorosilane, vinylmethyldichlorosilane, vinyldimethylchlorosilane, vinyldimethylmethoxysilane, vinyltrimethylsilane, divinyldichlorosilane, divinyldimethoxysilane, divinyldimethylsilane, 1,3-divinyl-1,1,3,3-tetramethyldisiloxane, trivinylmethylsilane, γ-methacryloyloxypropyltrimethoxysilane, and γ-methacryloyloxypropylmethyldimethoxysilane);
- vinylcarbazole;
- β-pinene;
- acenaphthylene; and
- like monomers.

These may be used singly or two or more of them may be used in combination. From the viewpoint of balanced physical properties and polymerization characteristics, among others, the use of aromatic vinyl monomers as the constituents is preferred.

The block structure of the isobutylene block copolymer of the blend is not particularly restricted and thus can be a diblock copolymer, a triblock copolymer, a multiblock copolymer and the like having a straight chain, branched chain, star-shaped or other structure. As block copolymers preferred from the balanced physical properties and polymerization characteristics, among others, there may be mentioned, for example, triblock copolymers composed of a polymer block derived from an aromatic vinyl monomer as the constituent/a polymer block derived from isobutylene as the constituent/a polymer block derived from an aromatic vinyl monomer as the constituent, diblock copolymers composed of a polymer block derived from an aromatic vinyl monomer as the constituent/a polymer block derived from isobutylene as the constituent, and star-shaped block copolymers having at least three arms each composed of a polymer block derived from an aromatic vinyl monomer as the constituent and a polymer block derived from isobutylene as the constituent. It is possible to use these either singly or in combination of two or more species so that the desired physical properties and moldability/processability may be obtained. Among them, the triblock copolymers and diblock copolymers mentioned above are preferred, and styrene-isobutylene-styrene triblock copolymers (SIBS) or styrene-isobutylene diblock copolymers, in which styrene is used as the aromatic vinyl monomer, are more preferred.

The relative concentration of the polymer block component (a) and the polymer block component (b) as part of the isobutylene block copolymer of the polymer blend can be varied to provide for desired flexibility and physical properties. In the preferred embodiment, the mole fraction of the polymer block component (b) as part of the isobutylene block copolymer is preferably between 15% and 45% (and more preferably between 25% and 35%), and the mole fraction of the polymer block component (a) as part of the isobutylene block copolymer is preferably between 85% and 55% (and more preferably between 75% and 65%). Moreover, the Shore hardness of the isobutylene block copolymer of the polymer blend is preferably between 70A and 90A (and more particularly on the order of 80A).

The molecular weight of the isobutylene block copolymer of the blend is not particularly restricted but, from the viewpoint of flowability, processability and physical properties, among others, the weight average molecular weight is preferably 30,000 to 500,000, more preferably 50,000 to 200,000, still more preferably 50,000 to 150,000. When the weight average molecular weight of the isobutylene block copolymer is lower than 30,000, there is a tendency toward tackiness (feel of tack) and the desired mechanical properties are not expressed to a sufficient extent. When, on the other hand, it exceeds 500,000, disadvantages will be experienced from the flowability and processability viewpoint.

The method of producing the isobutylene block copolymer of the blend is not particularly restricted but the copolymer can be obtained, for example, by polymerizing a monomer component derived from isobutylene and a monomer component derived from a monomer other than isobutylene in the presence of a compound represented by the general formula:

$$(CR^1R^2X)_nR^3 \qquad (1)$$

In the above formula, X is a substituent selected from among halogen atoms and alkoxy or acyloxy groups containing 1 to 6 carbon atoms (preferably 1 to 3 carbon atoms). $R^1$ and $R^2$ are each independently is a hydrogen atom or a monovalent hydrocarbon group containing 1 to 6 carbon atoms (preferably 1 to 3 carbon atoms). $R^1$ and $R^2$ may be the same or different. $R^3$ is a mono- to hexavalent aromatic or alicyclic hydrocarbon group or a mono- to tetravalent aliphatic hydrocarbon group, and n represents a natural number of 1 to 6 when the $R^3$ group is an aromatic or alicyclic hydrocarbon group and, when the $R^3$ group is an aliphatic group, n represents a natural number of 1 to 4.

The compound represented by the formula (1) serves as an initiator and presumably forms a carbocation in the presence of a Lewis acid or the like, which serves as an initiation site for cationic polymerization. Among them, compounds wherein $R^3$ group in formula (1) is a mono- to trivalent aromatic hydrocarbon group are preferred.

During the polymerization of the isobutylene block copolymer, a Lewis acid catalyst may further be caused to coexist. Such Lewis acid catalyst may be any of those which can be used in cationic polymerization, including metal halides (such as $TiCl_4$, $TiBr_4$, $BCl_3$, $BF_3$, $BF_3 \cdot OEt_2$, $SnCl_4$, $SbCl_5$, $SbF_5$, $WCl_6$, $TaCl_5$, $VCl_5$, $FeCl_3$, $ZnBr_2$, $AlCl_3$ and $AlBr_3$), organometal halides (such as $Et_2AlCl$ and $EtAlCl_2$). The addition amount of the Lewis acid is not particularly restricted but can be selected according to the polymerization characteristics of the monomers employed and/or the polymerization concentration, among others. Generally, the Lewis acid can be used at amounts of 0.1 to 100 mole equivalents, preferably 1 to 50 mole equivalents, relative to 1 mole of the compound represented by the general formula (1).

In polymerizing the isobutylene block copolymer, an electron donor component may be used as desired. This electron donor component is considered to be effective in stabilizing the growing carbocations on the occasion of cationic polymerization and, when such an electron donor is added, a structurally controlled polymer with a narrow molecular weight distribution is formed. The electron donor component to be used is not particularly restricted but includes, for example, pyridines, amines, amides, sulfoxides, esters, and metal compound containing a metal atom-bound oxygen atom(s), among others.

The polymerization reaction for producing the isobutylene block copolymer can be carried out in an organic solvent. The organic solvent is not particular restricted provided that it will not essentially disturb the cationic polymerization. As specific example of the organic solvents, there may be mentioned, among others, halogenated hydrocarbons such as methyl chloride, dichloromethane, chloroform, ethyl chloride, dichloroethane, n-propyl chloride, n-butyl chloride and chlorobenzene; benzene and alkylbenzenes such as toluene, xylene, ethylbenzene, propylbenzene and butylbenzene; straight chain aliphatic hydrocarbons such as ethane, propane, butane, pentane, hexane, heptane, octane, nonane and decane; branched aliphatic hydrocarbons such as 2-methylpropane, 2-methylbutane, 2,3,3-trimethylpentane and 2,2,5-trimethylhexane; cyclic aliphatic hydrocarbons such as cyclohexane, methylcyclohexane and ethylcyclohexane; and paraffin oils derived from petroleum fractions by purification by hydrogenation.

The polymerization reaction for producing the isobutylene block copolymer is preferably carried out in a controlled temperature range between $-100°$ C. and $0°$ C. (most preferably in a range between $-80°$ C. and $-30°$ C.).

These relative concentrations of the isobutylene block copolymer and the thermoplastic polyurethane elastomer of the blend can be adjusted to control the tensile strength and degree of hydrophobicity of the blend. The mole fraction of the isobutylene block copolymer as part of the polymer blend can range from 1% to 50%. In the preferred embodiment, the mole fraction of the isobutylene block copolymer of the polymer blend is in the range of 2% to 15% (and more preferably on the order of 10%), and the mole fraction of the thermoplastic polyurethane elastomer of the blend is in the range of 98% to 85% (and more preferably on the order of 90%). In the preferred embodiment, the polymer blend has a maximum tensile strength in the range between 20 and 40 MPa (and more preferably in the range between 25 MPa and 35 MPa). The maximum tensile strength of the polymer blend is the maximum stress on the stress-strain curve, which can be measured by subjecting a sample of the polymer blend to pull testing in a tension tester (for example, a tension tester sold commercially by Instron Corp. of Norwood, Mass.). In the preferred embodiment, the hardness of the polymer blend can be characterized by a Shore hardness in a range between 70A and 80A. Shore hardness is measured by a Shore durometer (for example, a Shore durometer sold commercially by Instron Corp. of Norwood, Mass.), which typically includes a diamond-tipped hammer that is allowed to fall from a known height onto the test specimen. The hardness number depends on the height to which the hammer rebounds; the harder the material, the higher the rebound. In the preferred embodiment, the elastic characteristics of the isobutylene block copolymer and the thermoplastic polyurethane elastomer of the blend are similar so as to provide a smooth stress/strain curve. Moreover, if blended by melt processing, the melting points of the isobutylene block copolymer and the thermoplastic polyurethane elastomer of the blend are in the same range to avoid one polymer burning before the other is melted.

In addition, some polyurethanes demonstrate better compatibility with isobutylene block copolymer than others. For example, polyether urethane using MDI as the diisocyanate, polytetramethylene glycol as the macroglycol and 1,4-butanediol as the chain extender when blended with SIBS of 20 mole percent styrene, provides a clear transparent polymer.

On the other hand, a polycarbonate urethane comprised of MDI, poly(tetramethylene carbonate)glycol and 1,4-butanediol bended with SIBS provides a white opaque polymer. Therefore, for certain applications where transparency is required the aromatic polyether urethane is preferred. Compatibilizers such as polyisobutylene capped with polyurethane groups can also be added to the blend to help render the SIBS more compatible with the polyurethane.

Other polymeric components and/or additives can be included in the blend polymer. The additives can include lubricants, antioxidants, UV stabilizers, melt processing aids, extrusion processing aids, blocking agents, pigments, radioopaques, fillers and the like. The lubricants can be fatty acid type lubricants, paraffin type lubricants or combination thereof. The fatty acid type lubricants can include a fatty acid metal salt type lubricant, a fatty acid amide type lubricant, a fatty acid ester type lubricant, an aliphatic alcohol type lubricant, a fatty acid-polyhydric alcohol partial ester and/or combinations thereof. The paraffin type lubricant can include a paraffin wax, a liquid paraffin, a polyethylene wax, an oxidized polyethylene wax, a polypropylene wax and/or combinations thereof.

Blending of the isobutylene block copolymer and the thermoplastic polyurethane elastomer can be performed by mixing together the polymers in a melt or by mixing the polymers in solution. Melt blending can be carried out in a hot mixing machine such as a single-screw extruder, twin-screw extruder, Brandbury mixer, Brabender mixer, or a high-shear mixer. Both polymers are heated together until sufficiently soft to allow mixing, which is preferably accomplished at temperature between 150° C. and 200° C. Blending in solution can be carried out is a suitable solvent. For example, most isobutylene block copolymers and polyurethane elastomers are soluble in tretrahydrofuran (THF). Therefore, for example purposes only, a 15% solution of polyether urethane in THF can be mixed with a 15% solution of SIBS to provide a blended polymer. The solvent can then be flashed off or the polymer can be precipitated from solution by the addition of copious amounts of isopropyl alcohol. The blends so formed can be pelletized and processed for use as the outer insulating part 15 and the inner insulating part 17 of the lead body as described herein.

Importantly, the polymer blend of the outer insulating part 15 and the inner insulating part 17 of the lead body is less permeable to oxygen relative to polyurethane alone due to the oxygen permeability characteristics of the isobutylene block copolymer of the blend. The measure of oxygen permeability of a material is in non-SI units called "Barrers". These units were defined by (and are important to the contact lens industry) because the supply of oxygen to the cornea is mandatory for survival of the cornea and the comfort of the wearer. Most polymers have a Barrer number of approximately 25 to 35. Polyurethane has a Barrer number in the range of 25-30. The polymer blend of the present invention has a Barrer number in the range of 15-25. The reduced oxygen permeability characteristics of the polymer blend as part of both the outer insulating structure 15 and the inner insulating structure 17 of the lead body thus limits oxygen flow through the insulating structures to the metal conductor from inside (i.e., from the inside channel) and from outside the lead body and thus provides improved resistance to MIO and ESC while maintaining the flexibility and desired tensile strength of the insulating structure (parts 15, 17) of the lead body.

The inner insulating part 17 can be formed by dip coating, spraying or co-extrusion over a core with the flexible conductor element(s) 13 wound about the inner insulating part 17. The outer insulating part 15 can be formed by dip coating, spraying or co-extrusion over the resultant structure. The core is then removed to provide the lead body as shown. Details of exemplary processing for producing this structure is set forth in U.S. Pat. No. 4,484,586 to McMikle et al., herein incorporated by reference in its entirety.

There have been described and illustrated herein several embodiments of an improved pacemaker lead body and methods of constructing same. While particular embodiments of the invention have been described, it is not intended that the invention be limited thereto, as it is intended that the invention be as broad in scope as the art will allow and that the specification be read likewise. Thus, while particular constituent elements have been disclosed for the isobutylene block copolymer of the blend, it will be appreciated that other isobutylene derived constituents can be used as well. For example, in an alternate embodiment, polyisobutylene of molecular weight greater than 1,000 Daltons can be used as a substitute for the isobutylene block copolymer of the blend. In addition, while particular configurations of the pacemaker lead body have been disclosed, it will be understood that the polymer blend of the present invention can be used in other configurations. For example, and not by way of limitation, it is contemplated that the inner insulating part can be omitted and/or formed as a solid core and/or formed from a different polymer material. In yet other embodiments, multi-axial configurations can be provided where multiple flexible conductors are concentrically spaced apart radially from one another between insulating structures. An example of such a structure is illustrated in FIG. 2 of U.S. Pat. No. 7,555,349, herein incorporated by reference in its entirety. In another embodiment, configurations can be provided where multiple flexible conductors are non-concentrically spaced apart and protected by surrounding insulating structure(s). Examples of such configurations are disclosed in U.S. Pat. Nos. 5,545,203 and 5,584,873, herein incorporated by reference in their entireties. It will therefore be appreciated by those skilled in the art that yet other modifications could be made to the provided invention without deviating from its spirit and scope as claimed.

What is claimed is:

1. A flexible pacemaker lead comprising:
    a lead body supporting at least one flexible conductor element that provides an electrical signal path between a proximal connector element and a distal electrode, said lead body including an insulating structure that protects said at least one flexible conductor element, said insulating structure realized from a polymer blend of a thermoplastic polyurethane elastomer and an isobutylene block copolymer, wherein mole fraction of said isobutylene block copolymer as part of said polymer blend in a range between 2% and 15%, and said polymer blend has a maximum tensile strength in the range between 20 MPa and 40 MPa;
    wherein said isobutylene block copolymer of said polymer blend consists of a first polymer block component containing isobutylene-derived monomer units and a second polymer block component derived from a monomer component other than isobutylene; and
    wherein said second polymer block component comprises at least one cation-polymerizable monomer selected from the group including aliphatic olefins, alicyclic olefins, aromatic vinyl compounds, dienes, vinyl ethers, silanes, vinylcarbazole, β-pinene, acenaphthylene and like monomers.

2. A flexible pacemaker lead according to claim 1, wherein:
    said at least one flexible conductor element comprises a coiled wire conductor defining a central axis with an outer surface facing radially outward away from the central axis and an inner surface facing radially inward toward the central axis; and said insulating structure surrounds at least said outer surface of said coiled wire conductor.

3. A flexible pacemaker lead according to claim 2, wherein: said insulating structure encapsulates said coiled wire conductor.

4. A flexible pacemaker lead according to claim 3, wherein: said insulating structure comprises a coaxial insulting structure including an outer insulating part and an inner insulating part.

5. A flexible pacemaker lead according to claim 4, wherein: said at least one flexible conductor element is formed over said inner insulating part, and said outer insulating part is formed over both said at least one flexible conductor and said inner insulating part.

6. A flexible pacemaker lead according to claim 4, wherein: said inner insulating part defines a guide lumen for receiving a stylet.

7. A flexible pacemaker lead according to claim 1, wherein: said thermoplastic polyurethane elastomer of said polymer blend comprises soft segments, an isocynate component, and an optional chain extender component.

8. A flexible pacemaker lead according to claim 7, wherein: said soft segments are selected from the group including polyesters, polyethers, aliphatics, polycarbonates and mixtures thereof.

9. A flexible pacemaker lead according to claim 7, wherein: said soft segments comprise macrodiols terminated with diols, triols, multiols, or combinations thereof.

10. A flexible pacemaker lead according to claim 7, wherein: said soft segments comprise macroamines terminated with diamines, triamines, multiamines, or combinations thereof.

11. A flexible pacemaker lead according to claim 7, wherein: said isocyanate component comprises a diisocyanate selected from the group including methylene bisphenyl-diisocyanate (MDI), hydrogenated methylenebisphenyl diisocyanage (HMDI), toluene diisocyanate (TDI) hexamethylene dissocyanate, isophorone diisocyanate, and the like.

12. A flexible pacemaker lead according to claim 7, wherein: said optional chain extender components is selected from the group including 1,4-butanediol, ethylene glycol, ethylene diamine, 1,6-hexandiol and the like.

13. A flexible pacemaker lead according to claim 1, wherein: said isobutylene block copolymer of said polymer blend has a block structure selected from the group including a diblock copolymer structure, a triblock copolymer structure, and a multiblock copolymer structure.

14. A flexible pacemaker lead according to claim 13, wherein: said block structure has a straight chain, branched chain, star-shaped or other structure.

15. A flexible pacemaker lead according to claim 1, wherein: said isobutylene block copolymer of said polymer blend comprises a styrene-isobutylene-styrene triblock copolymer.

16. A flexible pacemaker lead according to claim 1, wherein: mole fraction of said first polymer block component as part of said isobutylene block copolymer is in a range between 15% and 45%.

17. A flexible pacemaker lead according to claim 1, wherein: said polymer blend is formed by melt mixing or mixing in solution.

18. A flexible pacemaker lead according to claim 1, wherein: mole fraction of said isobutylene block copolymer as part of said polymer blend is on the order of 10%.

19. A flexible pacemaker lead according to claim 1, wherein: said polymer blend has a Shore hardness between 70A and 80A.

* * * * *